(12) United States Patent
Cahen

(10) Patent No.: US 8,455,417 B2
(45) Date of Patent: Jun. 4, 2013

(54) PERSONAL CARE COMPOSITIONS WITH IMPROVED HYPOSENSITIVITY

(75) Inventor: Christine Marie Cahen, Virginia Water (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/536,050

(22) Filed: Jun. 28, 2012

(65) Prior Publication Data

US 2012/0270932 A1 Oct. 25, 2012

Related U.S. Application Data

(63) Continuation of application No. 11/144,313, filed on Jun. 3, 2005, now abandoned.

(30) Foreign Application Priority Data

Jul. 2, 2004 (EP) .................................... 04253993

(51) Int. Cl.
*C11D 3/50* (2006.01)

(52) U.S. Cl.
USPC .......................................... 510/106; 510/131

(58) Field of Classification Search
USPC ................................. 510/106, 131
See application file for complete search history.

(56) References Cited

U.S. PATENT DOCUMENTS

| | | | |
|---|---|---|---|
| 3,929,678 A | 12/1975 | Laughlin et al. | |
| 4,250,117 A | 2/1981 | Takahashi et al. | |
| 5,298,238 A | 3/1994 | Hussein et al. | |
| 5,861,144 A * | 1/1999 | Peterson et al. | 424/65 |
| 6,103,241 A | 8/2000 | Hood | |
| 7,022,656 B2 | 4/2006 | Verrall et al. | |
| 2001/0032645 A1* | 10/2001 | Cronk et al. | 128/200.24 |
| 2003/0012830 A1 | 1/2003 | Small | |
| 2003/0083212 A1* | 5/2003 | Willard et al. | 510/137 |
| 2003/0113277 A1 | 6/2003 | Santi et al. | |
| 2003/0148914 A1 | 8/2003 | Dasque et al. | |
| 2003/0152649 A1* | 8/2003 | Frame | 424/725 |
| 2003/0224858 A1 | 12/2003 | Smith | |
| 2004/0142840 A1 | 7/2004 | De Buzzaccarini et al. | |

FOREIGN PATENT DOCUMENTS

| | | |
|---|---|---|
| EP | 1048293 A1 | 11/2000 |
| FR | 2748 204 A1 | 5/1996 |
| JP | 4128234 A2 | 4/1992 |
| WO | WO 98/22085 | 11/1997 |
| WO | WO 98/04241 A2 | 2/1998 |
| WO | WO 98/17229 A2 | 4/1998 |
| WO | WO 03/052040 A1 | 6/2003 |

OTHER PUBLICATIONS

Riaz et al., "The Chemical Composition of Pakistani Callistemon Citrinus Oils", J. Ess. Oil Res., 2, pp. 327-328, (Nov./Dec. 1990).
Chane-Ming et al., "Chemical Composition of Essential Oil of Callistemon Citrinus (Curtis) Skeel from Reunion", J. Essent. Oil Res., 10, pp. 429-431, (Jul./Aug. 1998).
Brophy et al., The Leaf Essential Oils of the Australian Members of the Genus Callistemon (Myrtaceae), J. Essent. Oil Res., 10, pp. 595-606, (Nov./Dec. 1998).
Srivastava et al., "Essential Oil Composition of Callistemon Citrinus Leaves from the Lower Region of Himalayas", J. Essent. Oil Res., 13, pp. 359-361 (Sep./Oct. 2001).
Jazet et al., "Correlation Between Chemical Composition and Antifungal Properties of Essential Oils of Callistemon Rigidus and Callistemon Citrinus of Cameroon Against Phaeoramularia Angolensis", Journal of Medicinal Plants Research, vol. 3(1), pp. 09-15, Jan. 2009.
Oyedeji et al., "Chemical Composition and Antibacterial Activity of the Essential Oils of Callistemon Citrinus and Callistemon Viminalis from South Africa", Molecules 2009, 14, pp. 1990-1998; doi:10.3390/molecules14061990.

* cited by examiner

*Primary Examiner* — John Hardee
(74) *Attorney, Agent, or Firm* — Alexandra S. Anoff

(57) ABSTRACT

The present invention provides personal care compositions comprising a carrier and a mixture of essential oil components having specific levels of eucalyptol, terpene materials and auxiliary fragrance materials. The compositions herein gentle to skin and have a fragrance and activity similar if the composition were made using the pure extracted essential oil.

20 Claims, No Drawings

PERSONAL CARE COMPOSITIONS WITH IMPROVED HYPOSENSITIVITY

CROSS REFERENCE TO RELATED APPLICATIONS

This application is a continuation of U.S. application Ser. No. 11/144,313, filed on Jun. 3, 2005, now abandoned.

FIELD OF THE INVENTION

The present invention relates to the field of personal care compositions comprising essential oils. More specifically, the present invention provides personal care compositions comprising a mixture of essential oil components having improved hyposensitivity whilst maintaining well-rounded fragrance characteristics and aromatherapeutic application.

BACKGROUND OF THE INVENTION

Many personal care compositions on the market today contain essential oils as fragrances, and more recently as active ingredients useful for the treatment of a variety of ailments. Such uses have been generated out of the interest associated with aromatherapy, in which various essential oils are vaporized and inhaled by the user. This practice has led to the use of rosemary and lavender oils for relaxation, eucalyptus and citrus oils for the treatment of respiratory infections, and a variety of other novel oils used as analgesics, muscle relaxants and the like.

Essential oils are a mixture of chemical entities, the majority of which are terpene-like materials. Each essential oil comprises a unique mixture of terpenes and other similar materials that provide the individual fragrance and activity of the essential oil. The composition of an essential oil is dependent not only upon the source of the oil, but also upon the method of extraction. Different extraction methods can generate essential oils having differing levels and ratios of important components, and this in turn can result in essential oils having different fragrance and activity profiles, despite being isolated from the same source.

A problem associated with essential oils is the fact that they can contain auxiliary fragrance materials some of which are recognized as potential allergens and/or irritating agents. These materials, in a proportion of the population, can cause hypersensitivity-type reactions, or skin irritation, manifested as skin redness, burning, itching, and in severe cases, edema and skin peeling. Unfortunately, these same auxiliary fragrance materials such as limonene, linalool, benzyl alcohol and geraniol in combination with terpenes such as—and -pinene and—phellandrene are typically fundamental to the fragrance of the essential oil and, in some instances, required for the purported aromatherapeutic activity of the oil in question. By simply eliminating these auxiliary fragrance materials in the essential oil, the oil typically does not meet the user's expectation in both fragrance impact and roundness and aromatherapeutic activity. Therefore, a need exists for personal care compositions comprising essential oils or materials thereof, which have improved allergen profiles. More precisely, a need exists for personal care compositions comprising essential oils that have reduced levels of auxiliary fragrance materials, but also a select level and ratio of these materials in combination with a base fragrance and specific terpene materials in order to deliver the fragrance and activity of the essential oil without associated sensitivity problems.

U.S. Pat. No. 5,298,238 to Hussein et al. discloses liquid oral compositions comprising deterpenated and fractionated peppermint oil. The compositions therein comprise very low levels of 1,8-cineole,—and -pinenes and linalool and limonene. US Application 2003/0012830 A1 discloses a topical composition comprising eucalyptol, -pinene and acetone. EP 1048293 A discloses head-lice treatment compositions comprising eucalyptol and limonene in water. WO 98/17749 discloses an essential oil extracted from the shrub Kunzea Ambigua which contains high levels of—and -pinenes. WO 98/17229 discloses medicaments comprising at least 25% eucalyptol, and at least 25% limonene. US Application 2003/0113277 A1 discloses oral care compositions comprising eucalyptol and limonene for masking the taste of phenolics such as triclosan present in the compositions. The above compositions either do not deliver the required reduced level of auxiliary fragrance materials to avoid sensitivity reactions and therefore are not hyposensitive formulae, or do not contain enough auxiliary fragrance materials to generate a well-rounded fragrance or associated aromatherapeutic activity.

It has been found that personal care compositions can be formulated with essential oil component materials that reconstitute the essential oil in the composition to maximize the fragrance and activity associated with the essential oils therein, whilst improving the hyposensitivity of the compositions by selectively blending the constituent fragrance materials. It has further been found that removing the auxiliary fragrance materials entirely lessens the impact of the essential oil, and that by incorporating these materials at low levels and in select ratios with other terpene materials, a mixture is generated having fragrance and activity similar to the pure extracted essential oil that is gentle to skin.

SUMMARY OF THE INVENTION

The present invention is directed towards providing personal care compositions comprising:
a) from 0.01% to 15% eucalyptol;
b) from 0.01% to 10% terpene material comprising -pinene, -pinene, -phellandrene, para-cymene or mixtures thereof;
c) from 0.0001% to 0.01% auxiliary fragrance material comprising amyl cinnamal, benzyl alcohol, cinnamal alcohol, citral, eugenol, hydroxy-citronellal, isoeugenol, amylcin-namyl alcohol, benzyl-salicylate, cinnamal, coumarin, geraniol, hydroxy-methylpentyl-cyclohexanecarboxaldehyde, anisyl alcohol, benzyl cinnamate, farnesol, 2(4-tert-butylbenzylpropionaldehyde), linalool, benzyl benzoate, citronellol, hexyl cinnam-aldehyde, limonene, methyl heptin carbonate, 3-methyl-4-(2,6,6-tri-methyl-2-cyclohexen-1-yl)-3-buten-2-one, or mixtures thereof;
d) a carrier.
The compositions herein are gentle to skin and have a fragrance and activity similar if the composition were made using the pure extracted essential oil.

DETAILED DESCRIPTION OF THE INVENTION

All weights, measurements and concentrations herein are measured at 25° C. on the composition in its entirety, unless otherwise specified.

Unless otherwise indicated, all percentages of compositions referred to herein are weight percentages and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore classifications herein are made for the sake of convenience and are not intended to limit an ingredient to the particularly stated application or applications listed.

The personal care compositions of the present invention comprise:
a) from 0.01% to 15% eucalyptol;
b) from 0.01% to 10% terpene material comprising -pinene, -pinene, -phellandrene, para-cymene or mixtures thereof;
c) from 0.0001% to 0.01% auxiliary fragrance material comprising amyl cinnamal, benzyl alcohol, cinnamal alcohol, citral, eugenol, hydroxy-citronellal, isoeugenol, amylcin-namyl alcohol, benzyl-salicylate, cinnamal, coumarin, geraniol, hydroxy-methylpentyl-cyclohexanecarboxaldehyde, anisyl alcohol, benzyl cinnamate, farnesol, 2(4-tert-butylbenzylpropionaldehyde), linalool, benzyl benzoate, citronellol, hexyl cinnam-aldehyde, limonene, methyl heptin carbonate, 3-methyl-4-(2,6,6-tri-methyl-2-cyclohexen-1-yl)-3-buten-2-one, or mixtures thereof;
d) a carrier.

The compositions herein are gentle to skin and have a fragrance and aromatherapeutic activity almost as if the composition were made using the pure extracted essential oil.

The personal care compositions of the present invention comprise a base fragrance material. The base fragrance material of the present invention comprises eucalyptol. Eucalyptol is also known as 1,8-cineole, and is a terpene-like material isolated from and named for eucalyptus essential oil. Eucalyptol is widely found in essential oils and used in synthetic fragrances in varying amounts. It is thought to be an important component of eucalyptus oil and other essential oils, and responsible for a wide variety of activities and fragrances associated therewith. Eucalyptol generally has a chemical structure as set out below:

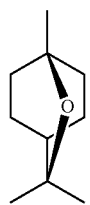

The personal care compositions of the present invention comprise from about 0.01% to about 15% eucalyptol. Preferably the personal care compositions herein comprise from about 0.1% to about 10%, more preferably from about 0.2% to about 8%, more preferably still from about 0.5% to about 5% eucalyptol by weight.

Eucalyptol is commercially available extracted from natural sources such as eucalyptus oil. Suitable examples of commercially available sources include eucalyptol available from Symrise (UK), Frey and Lau (UK) or FDL (UK).

The personal care compositions of the present invention further comprise a terpene material. Said terpene material comprises -pinene, -pinene, -phellandrene, para-cymene or mixtures thereof. Without wishing to be bound by theory, it is believed that the terpene material is useful herein, in combination with the allergenic fragrance material, for generating the characteristic fragrance notes, and providing effects such as relaxation, calming, muscle relaxation and analgesia associated with essential oils such as eucalyptus, rosemary and lavender.

The compositions of the present invention comprise from about 0.01% to about 10% terpene material, preferably from about 0.1% to about 6%, more preferably from about 0.5% to about 5% terpene material by weight, more preferably still from 0.5% to 4%.

The terpene materials according to the present invention correspond to the chemicals having the structure as set out in the table below.

| Name | Structure |
|---|---|
| -pinene | α-Pinen |
| -pinene | β-Pinen |
| -phellandrene | 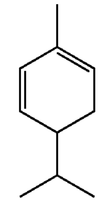 |
| Para-cymene | 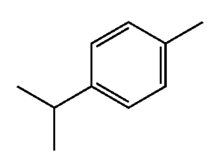 |

The personal care compositions of the present invention comprise from about 0.0001% to about 0.01% auxiliary fragrance material. The auxiliary fragrance material of the present invention comprises amyl cinnamal, benzyl alcohol, cinnamal alcohol, citral, eugenol, hydroxy-citronellal, isoeugenol, amylcin-namyl alcohol, benzyl-salicylate, cinnamal, coumarin, geraniol, hydroxy-methylpentylcyclohexanecarboxaldehyde, anisyl alcohol, benzyl cinnamate, farnesol, 2(4-tert-butylbenzylpropionaldehyde), linalool, benzyl benzoate, citronellol, hexyl cinnam-aldehyde, limonene, methyl heptin carbonate, 3-methyl-4-(2,6,6-tri-methyl-2-cyclohexen-1-yl)-3-buten-2-one, or mixtures thereof. Preferably said auxiliary fragrance material comprising limonene, linalool, benzyl alcohol, geraniol or mixtures thereof. Auxiliary fragrance materials are materials that are recognized as potentially potent allergens and/or irritating agents. These materials, in a proportion of the population, can cause hypersensitivity-type reactions, or skin irritation, manifested as skin redness, burning, itching, and in severe cases, edema and skin peeling. Unfortunately, these same materials are typically fundamental to the fragrance of the essential oil and, in some instances, required for the purported aromatherapeutic activity. However, simply removing these materials reduces the fragrance and effectives of the personal care composition. Without wishing to be bound by theory, it is believed that the compositions herein, by using these auxiliary fragrance materials at levels that typically do not generate sensitivity reactions, but whilst still being present in the composition, generates a subliminal fragrance change to the user, and is capable of providing the aromatherapeutic activities associated with pure essential oils.

The personal care compositions of the present invention preferably comprise from about 0.0001% to about 0.005% auxiliary fragrance materials, more preferably from about 0.0001% to about 0.001%. Preferably, the terpene material and the auxiliary fragrance material are formulated in the personal care compositions herein in ratios that enable the materials to act synergistically to provide fragrance and active benefits, whilst not generating a sensitivity-type response. Without being limited by theory, it is believed that both the auxiliary fragrance materials and terpene materials are essential to elicit the consumer response to essential oils, however, the combination herein allows the amount of auxiliary fragrance material present to be limited whilst still providing fragrance and active benefits. Preferably the ratio of terpene material to auxiliary fragrance material is from about 1:1 to about 1:10000, more preferably from about 1:10 to about 1:1000.

The personal care compositions of the present invention further comprise a carrier. The carrier may be any material capable of carrying and delivering the fragrance materials herein in a stable and consumer-aesthetic form. Such carriers must also be suitable for application to the skin, hair, oral mucosa, preferably the skin (i.e. topical application), more preferably sensitive skin such as that of a baby. Suitable carriers include water, $C_2$ to $C_6$ monohydric alcohols, petrolatum, fluid silicone materials such as dimethicones, or mixtures thereof. Preferred carriers herein include water, petrolatum, or mixtures thereof. Preferably, the compositions of the present invention comprise from about 1% to about 99.9799% carrier, more preferably from about 40% to about 95%, more preferably still from about 50% to about 93% carrier.

The personal care compositions of the present invention may be in any form suitable for consumer use. The compositions may be formulated as a leave-on composition or a rinse-off composition. As used herein, "leave-on compositions" includes products that are intended to be applied to a bodily surface of a consumer such as the skin or hair and maintained on the surface for a prolonged time, preferably at least 5 minutes, more preferably at least 30 minutes, without being actively removed by washing, rinsing, wiping, rubbing or other forms of mechanical removal. As used herein, "rinse-off compositions" includes compositions that are intended to be applied to a bodily surface of a consumer, such as the skin or hair, and subsequently removed by washing, rinsing, wiping, rubbing or other forms of mechanical removal within less than 5 minutes of application. Preferably, the composition is a leave-on composition.

The personal care composition of the present invention may be formulated as a lotion, an aerosol, a cream, a gel, a, liquid, a viscous liquid, or a paste. Alternatively, the compositions herein may comprise a patch that can be applied to the user's body or clothing. Preferably, such patches comprise an adhesive layer that enables attachment to the user's body or clothing. In a further alternative embodiment, the compositions herein need not be applied directly to the user's body or clothing, but rather be applied to an object that is positioned near to the user. This type of delivery method comprises dispensing the composition either as a series of droplets or via atomization (i.e. aerosol) onto a substrate such as the cloth of a pillow case, or a handkerchief. As used herein, "liquid" includes compositions having a viscosity of less than 10 mPa·s at 25° C. As used herein, "viscous liquid" means a liquid composition that has a viscosity of from about 10 mPa·s to about 300000 mPa·s when measured at 25° C., more prefereably from 50 mPa·s to 150 000 mPa·s. Viscosity herein is measured on neat composition using a Brookfield RVT, T-C Spindle at 5 rpms and Heliopath Stand. Viscous liquid compositions have a viscosity that is greater than that of water, and typically provide improved application characteristics when compared with products having a viscosity similar to that of water when applied directly by the user using manual (i.e. hand) application. Liquid compositions are preferable when dispensed as an aerosol or droplets. Preferably the personal care compositions of the present invention are a liquid, viscous liquid or gel.

Where the carrier comprises water or other low viscosity, liquid material, it may be preferable to increase the viscosity of the composition by employing a thickening agent. The compositions of the present invention comprise from about 0.1% to about 5%, preferably from about 0.1% to about 3%, and more preferably from about 0.25% to about 2%, thickening agent by weight of the composition.

Suitable thickening agents include cellulose and derivatives such as cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, micro-crystalline cellulose, sodium cellulose sulfate, and mixtures thereof. Also useful herein are the alkyl-substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol™ CS Plus from Aqualon Corporation.

Other useful thickeners include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof. Also useful are acrylic acid/ethyl acrylate copolymers and the carboxyvinyl polymers sold by the B.F. Goodrich Company under the trademark of Carbopol resins. Suitable Carbopol resins are described in WO98/22085.

Preferred compositions of the present invention include a thickening agent selected from carboxylic acid polymers, crosslinked polyacrylates, polyacrylamides, xanthan gum and mixtures thereof, more preferably selected polyacrylamide polymers, xanthan gum and mixtures thereof. Preferred polyacrylamides are predispersed in a water-immiscible solvent such as mineral oil and the like, containing a surfactant (HLB from about 7 to about 10) which helps to facilitate water dispersibility of the polyacrylamide. Also preferred for use herein is the non-ionic polymer under the CTFA designation: polyacrylamide and isoparaffin and laureth-7, available under the trade name Sepigel 305 from Seppic Corporation. More preferred for use herein are the co-polymer compositions commercially available from BASF Corp. under the tradename Luvigel EM™ and the co-polymer compositions available from CIBA Speciality Chemicals, Macclesfield, UK, under the tradename Salcare SC91™.

The personal care compositions of the present invention may further comprise emollient materials including branched chain hydrocarbons having an weight average molecular weight of from about 100 to about 15,000, preferably from about 100 to 1000; compounds of formula I:

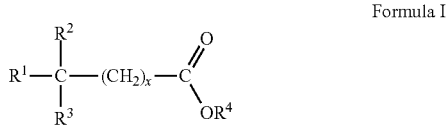

Formula I wherein $R^1$ is selected from H or $CH_3$, $R^2$, $R^3$ and $R^4$ are independently selected from $C_1$-$C_{20}$ straight chain or branched chain alkyl, and x is an integer of from 1-20; and compounds having the formula (II):

Formula II wherein $R^5$ is selected from optionally hydroxy or $C_1$-$C_4$ alkyl substituted benzyl and $R_6$ is selected from $C_1$-$C_{20}$ branched or straight chain alkyl; and mixtures thereof.

Suitable branched chain hydrocarbons for use herein include isododecane, isohexadecane, isoeicosane, isooctahexacontane, isohexapentacontahectane, isopentacontaoctactane, and mixture thereof. Suitable for use herein are branched chain aliphatic hydrocarbons sold under the trade name Permethyl™ and commercially available from Presperse Inc., P.O. Box 735, South Plainfield, N.J. 07080, U.S.A. Suitable ester emollient materials of Formula I above include, but are not limited to, methyl isostearate, isopropyl isostearate, isostearyl neopentanoate. isononyl isononanoate, isodecyl octanoate, isodecyl isononanoate, tridecyl isononanoate, myristyl octanoate, octyl pelargonate, octyl isononanoate, myristyl myristate, myristyl neopentanoate, myristyl octanoate, myristyl propionate, isopropyl myristate and mixtures thereof. Suitable ester emollient materials of Formula (II) include but are not limited to C12-15 alkyl benzoates.

Preferred emollients for use herein are isohexadecane, isononyl isononanoate, methyl isostearate, isopropyl isostearate, and mixtures thereof.

The emollient material is preferably present in the compositions at a level of from about 0.1% to about 10%.

The compositions herein may comprise an emulsifier and/or surfactant. For convenience hereinafter emulsifiers will be referred to under the term 'surfactants', thus 'surfactant(s)' will be used to refer to surface active agents whether used as emulsifiers or for other surfactant purposes such as skin cleansing. Known or conventional surfactants can be used in the composition, provided that the selected agent is chemically and physically compatible with essential components of the composition, and provides the desired characteristics.

The compositions of the present invention preferably comprise from about 0.05% to about 20% of a surfactant or mixture of surfactants. The exact surfactant or surfactant mixture chosen will depend upon the intended use, pH and the other components present in the composition. Surfactants suitable for use herein include anionic surfactants, cationic surfactants, zwitterionic surfactants, nonionic surfactants, or mixtures thereof.

Suitable nonionic surfactants useful herein are those that can be broadly defined as condensation products of long chain alcohols, e.g. $C_{8-30}$ alcohols, with sugar or starch polymers, i.e., glycosides. Preferred examples include a mixture of cetearyl glucosides and cetearyl alcohols such as those commercially available as Montanov 68™ from Seppic and Emulgade PL68/50™ available from Henkel.

Other useful nonionic surfactants include the condensation products of alkylene oxides with fatty acids (i.e. alkylene oxide esters or diesters of fatty acids). Other nonionic surfactants are the condensation products of alkylene oxides with fatty alcohols (i.e. alkylene oxide ethers of fatty alcohols). Still other nonionic surfactants are the condensation products of alkylene oxides with both fatty acids and fatty alcohols. Still other useful nonionic surfactants include poly-hydroxy fatty acid amide surfactants, which are described in more detail in WO98/04241. Other nonionic surfactants suitable for use herein include sugar esters and polyesters, alkoxylated sugar esters and polyesters, $C_1$-$C_{30}$ fatty acid esters of $C_1$-$C_{30}$ fatty alcohols, alkoxylated derivatives of $C_1$-$C_{30}$ fatty acid esters of $C_1$-$C_{30}$ fatty alcohols, alkoxylated ethers of C1-C30 fatty alcohols, poly-glyceryl esters of $C_1$-$C_{30}$ fatty acids, $C_1$-$C_{30}$ esters of polyols, $C_1$-$C_{30}$ ethers of polyols, alkyl phosphates, polyoxyalkylene fatty ether phosphates, fatty acid amides, acyl lactylates, and mixtures thereof. Other nonionic surfactants useful herein are fatty acid ester blends based on a mixture of sorbitan or sorbitol fatty acid ester and sucrose fatty acid ester, the fatty acid in each instance being preferably $C_8$-$C_{24}$, more preferably $C_{10}$-$C_{20,}$ commercially available examples of which include Arlatone 2121™ available from ICI.

Anionic surfactants are also useful in the present compositions. See, e.g., U.S. Pat. No. 3,929,678, to Laughlin et al., issued Dec. 30, 1975. Exemplary anionic surfactants include the alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilising group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, alkyl sarcosinates (e.g., $C_{12}$-$C_{30}$), and alkanoyl sarcosinates.

Emulsions of the present invention may include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. Other examples include alkyl-modified dimethicone copolyols, i.e., compounds that contain $C_2$-$C_{30}$ pendant side chains. Still other useful dimethicone copolyols include materials having various cationic, anionic, amphoteric, and zwitterionic pendant moieties.

The personal care compositions of the present invention may further comprise chamomile oil. Chamomile oil is useful in the present invention where the personal care composition is intended for use with babies or infants. Chamomile oil is hypoallergenic, and provides a soothing fragrance that babies and infants find pleasant. The personal care compositions preferably comprise from 0.0001% to 2% chamomile oil. Commercially available sources of chamomile oil include Bontou (FR), Payan & Betrand (FR) and Citrus & Allied (US).

The personal care compositions of the present invention may further include other perfume or fragrance materials that are acceptable to consumers, whilst not altering the hyposensitivity profile of the compositions herein. Suitable perfume or fragrance materials are known to those skilled in the art including chemical musk compounds, chemical wood compounds, chemical powder compounds, and chemical floral compounds. Non-limiting examples of fragrance materials suitable for use herein include cajeput oil, fennel oil, geranium oil, girfole oil, lemon oil, spearmint oil, myrtle oil, oregano oil, pine oil, sarriette oil, thyme oil, tea-tree oil or mixtures thereof. Furthermore, fragrance materials may further comprise the chemical constituents of essential oils such as vanillin, ethyl vanillin, musk, methyl-dihydro-jasmonate, anethol, catechole, camphene, ferulic acid, farnesol, hinokitiol, tropolone, menthol, methyl salicylate, carvacol, terpineol, verbenone, berbinene, ratanhiae extract, caryophellene oxide, citronella acid, curcumin, nerolidol or mixtures thereof. These materials may be used at levels and ratios known to those skilled in the art of mixing fragrance materials for personal care compositions, whilst maintaining the levels of base fragrance comprising eucalyptol, terpene materials and auxiliary fragrance materials according to the present invention.

The personal care compositions of the present invention may further comprise active ingredients. Suitable active ingredients include skin benefit agents, analgesics, anesthetics, neutralizing agents, sunscreening agents or mixtures thereof. The compositions of the present invention preferably comprise from about 0.01% to about 20% of these active ingredients.

Analgesic, antipyretic and anti-inflammatory agents useful herein include, but are not restricted to the group comprising acetaminophen, aspirin, diclofenac, diflunisal, etodolac, fenoprofen, flurbiprofen, ibuprofen, ketoprofen, ketorolac, nabumetone, naproxen, piroxicam, caffeine, eugenol, thymol, or mixtures thereof. Local anesthetics useful herein include lidocaine, benzocaine, phenol, dyclonine, benzonotate, or mixtures thereof.

Water-soluble skin benefit agents useful herein include vitamin $B_3$ compounds, humectants, amino acids, vitamin C compounds, panthenol and derivatives, or mixtures thereof. Suitable oil soluble actives for use herein include vitamin E and its derivatives, salicylic acid and other beta-hydroxy acids, perfumes and occlusion materials, and mixtures thereof.

Another optional ingredient is neutralizing agents. Neutralizing agents suitable for use in neutralizing acidic groups containing hydrophilic gelling agents herein include sodium hydroxide, potassium hydroxide, ammonium hydroxide, monoethanolamine, diethanolamine, amino methyl propanol, tris-buffer and triethanolamine.

A further optional component may comprise sunscreening agents. Preferred among those sunscreens which are useful in the compositions of the invention are those selected from 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, Parsol MCX, Eusolex 6300, Octocrylene, Parsol 1789, and mixtures thereof.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206-38269, Aug. 25, 1978.

The personal care compositions herein are preferably in the form of an emulsion, such as a water-in-oil or oil-in-water emulsion. The oil phase may contain different materials, or different combinations of materials, or may contain multiple oil phases. The total level of oil phase components in the compositions of the invention is typically from about 0.1% to about 60%, preferably from about 1% to about 30%, more preferably from about 3% to about 20% and most preferably from about 5% to about 15%.

In preferred embodiments, the oil phase preferably comprises oily components such as a natural or synthetic oils selected from mineral, vegetable, and animal oils, fats and waxes, fatty acid esters, fatty alcohols, fatty acids and mixtures thereof. Preferred for use herein are for example, saturated and unsaturated fatty alcohols such as behenyl alcohol, cetyl alcohol and stearyl alcohol and hydrocarbons such as mineral oils.

Preparation

The personal care compositions of the present invention are prepared typically as "reconstituted essential oils" dispersed in a carrier. The term "reconstituted essential oils" herein includes essential oils that are generated by mixing together individual raw materials in levels and ratios that, when dispersed in the composition, correspond to the levels of the present invention. Furthermore, "reconstituted essential oils" includes fractionated essential oils that have had the majority of the terpene materials and auxiliary fragrance materials removed such as those disclosed in U.S. Pat. No. 5,298,238 which have then had the terpene materials and auxiliary fragrance materials added back into the essential oil base (comprising eucalyptol) and then dispersed in a carrier at the levels according to the present invention. Furthermore, the compositions of the present invention may be prepared using essential oils that have been specifically fractionated to provide levels of eucalyptol, terpene materials comprising -pinene, -pinene, -phellandrene or mixtures thereof, and auxiliary fragrance materials according to the present invention when dispersed in the carrier of the personal care composition.

EXAMPLES

The following examples were manufactured using techniques known to those skilled in the art. The base fragrance (eucalyptol), terpene materials and auxiliary fragrance materials were blended together separately before being added to the compositions to give the final amounts specified. The following examples are illustrative only, and not intended to limit the scope of the present invention.

| Ingredient | Ex. 1 (% wt) | Ex. 2 (% wt) | Ex. 3 (% wt) | Ex. 4 (% wt) | Ex. 5 (% wt) | Ex. 6 (% wt) |
|---|---|---|---|---|---|---|
| Petrolatum | q.s. 100 | q.s. 100 | q.s. 100 | — | — | 10 |
| Water | — | — | — | q.s. 100 | q.s. 100 | q.s. 100 |
| Ethanol | — | — | — | — | — | 20 |
| Eucalyptol | 6.655 | 0.7 | 1.305 | 0.25 | 0.45 | 5.00 |
| pinene | 2.5 | 0.5 | 0.3 | 0.05 | 0.1 | 1.3 |
| pinene | 0.3 | 0.01 | 0.3 | 0.05 | 0.05 | 1.5 |
| phellandrene | — | — | 0.01 | 0.01 | — | 0.5 |
| Limonene | 0.003 | 0.0006 | 0.0003 | 0.01 | — | 0.008 |
| Linalool | 0.0001 | 0.0001 | 0.0003 | — | 0.0005 | 0.001 |
| Benzyl Alcohol | — | — | — | — | 0.0001 | — |
| Geraniol | — | — | — | — | 0.0002 | 0.001 |
| Chamomile Oil | 0.0001 | — | 0.15 | 0.10 | — | — |
| Sodium Laureth-3-Sulfate | — | — | — | 11.80 | 11.80 | — |
| Cocamidopropyl Betaine | — | — | — | 3.25 | 3.25 | — |
| Sodium Lauroyl Sarcosinate | — | — | — | 0.50 | 0.50 | — |
| Polyquaternium-10 | — | — | — | 0.10 | 0.10 | — |
| PEG-200 Glyceryl Palmate | — | — | — | 1.00 | 1.00 | — |
| Potassium Sorbate | — | — | — | 0.25 | 0.25 | — |
| Sodium Benzoate | — | — | — | 0.25 | 0.25 | 0.1 |
| Citric Acid Anhydrous | — | — | — | 0.30 | 0.30 | — |
| Sodium Citrate | — | — | — | 1.00 | 1.00 | — |

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modification can be made without departing from the spirit and scope of the invention. It is therefore intended to cover in the appended claims all such changes and modifications that are within the scope of this invention.

What is claimed is:

1. A hypoallergenic personal care composition comprising:
   a. from about 0.25% to about 15% of eucalyptol;
   b. from about 0.61% to about 10% of a terpene material selected from the group consisting of α-pinene, β-pinene, α-phellandrene, para-cymene and mixtures thereof; and
   c. a hypoallergenic amount, from about 0.0001% to about 0.01%, of an auxiliary fragrance material selected from the group consisting of linalool, limonene, and mixtures thereof;
   wherein said composition is adapted for topical administration to babies and infants.

2. The personal care composition according to claim 1 comprising from about 0.25% to about 6.65% eucalyptol.

3. The personal care composition according to claim 1 wherein the terpene material is α-pinene.

4. The personal care composition according to claim 1 comprising from about 0.61% to about 2.5% terpene material.

5. The personal care composition according to claim 1 comprising from about 0.0001% to about 0.005% auxiliary fragrance material.

6. The personal care composition according to claim 1 comprising reconstituted essential oils.

7. The personal care composition according to claim 1 wherein the composition is selected from the group consisting of a viscous liquid, gel, paste, and combinations thereof.

8. The personal care composition according to claim 1 wherein the composition is a leave-on product.

9. A method of administering the personal care composition according to claim 1 comprising:
   a. providing the personal care composition of claim 1; and
   b. applying the personal care composition to skin of a healthy baby or infant.

10. The method according to claim 9 wherein the personal care composition is gentle to a baby or infant's skin.

11. A method of relaxing a baby or infant comprising:
    a. providing the personal care composition of claim 1; and
    b. applying the personal care composition to skin of a baby or infant.

12. A method of providing aroma therapy comprising:
    a. providing the personal care composition of claim 1; and
    b. applying the personal care composition to skin of a baby or infant.

13. The method according to claim 12 wherein the personal care composition is gentle to a baby or infant's skin.

14. A method of calming a baby or infant comprising:
    a. providing the personal care composition of claim 1; and
    b. applying the personal care composition to skin of a baby or infant.

15. A method of soothing a baby or infant comprising:
    a. providing the personal care composition of claim 1; and
    b. applying the personal care composition to skin of a baby or infant.

16. A hypoallergenic personal care composition comprising:
    a. from about 0.25% to about 6.65% of eucalyptol;
    b. from about 0.61% to about 2.5% of a terpene material; and
    c. a hypoallergenic amount, from about 0.0001% to about 0.01% linalool;
    wherein said composition is adapted for topical administration to babies and infants.

17. The personal care composition according to claim 16 comprising reconstituted essential oils.

18. A method of soothing a baby or infant comprising:
   a. providing the personal care composition of claim 16; and
   b. applying the personal care composition to skin of a baby or infant.

19. A hypoallergenic personal care composition comprising:
   a. from about 0.25% to about 6.65% of eucalyptol;
   b. from about 0.61% to about 2.5% of a terpene material; and
   c. a hypoallergenic amount, from about 0.0001% to about 0.01% limonene;
      wherein said composition is adapted for topical administration to babies and infants.

20. A method of soothing a baby or infant comprising:
   a. providing the personal care composition of claim 19; and
   b. applying the personal care composition to skin of a baby or infant.

* * * * *